United States Patent
Cahan (10) Patent No.: US 11,197,956 B2
(45) Date of Patent: Dec. 14, 2021

(54) PORTAL SYSTEM-BASED BIONIC PANCREAS

(71) Applicant: INTERNATIONAL BUSINESS MACHINES CORPORATION, Armonk, NY (US)

(72) Inventor: Amos Cahan, Dobbs Ferry, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 52 days.

(21) Appl. No.: 16/691,741

(22) Filed: Nov. 22, 2019

(65) Prior Publication Data

US 2020/0086048 A1  Mar. 19, 2020

Related U.S. Application Data

(62) Division of application No. 15/239,262, filed on Aug. 17, 2016.

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 5/14276* (2013.01);
(Continued)

(58) Field of Classification Search
CPC ............ A61B 5/14532; A61B 5/14503; A61B 5/0002; A61B 5/14865; A61M 5/1723;
(Continued)

(56) References Cited

U.S. PATENT DOCUMENTS

| 4,822,337 A | 4/1989 | Newhouse et al. |
| 6,176,838 B1 * | 1/2001 | Sase ...................... A61B 6/481 |
| | | 600/431 |

(Continued)

FOREIGN PATENT DOCUMENTS

| CN | 101874911 A | 11/2010 |
| CN | 202409794   | 9/2012  |
| CN | 102836481 B | 8/2014  |

OTHER PUBLICATIONS

Burcelin R, et al. "Portal glucose infusion in the mouse induces hypoglycemia: evidence that the hepatoportal glucose sensor stimulates glucose utilization." Diabetes. Oct. 2000;49(10):1635-42. doi: 10.2337/diabetes.49.10.1635. PMID: 11016446. (Year: 2000).*

(Continued)

*Primary Examiner* — Scott J Medway
(74) *Attorney, Agent, or Firm* — Cantor Colburn LLP; Kristofer Haggerty (57) ABSTRACT

Embodiments include methods and systems for maintaining glucose homeostasis. Systems can include a pump, a first reservoir including a homeostasis agent, an umbilical catheter capable of being advanced in the umbilical vein or in the falciform ligament, and a sensor. Systems can also include a biocompatible coating, a microprocessor in communication with the pump and the sensor, and a power supply. Methods can include implanting a pump and reservoir subcutaneously in a patient, advancing a catheter in the umbilical vein or in the falciform ligament, measuring a blood glucose level, pumping a homeostasis agent, and administering the homeostasis agent to the portal venous system.

13 Claims, 8 Drawing Sheets

(52) U.S. Cl.
CPC ..... *A61M 2202/07* (2013.01); *A61M 2205/04* (2013.01); *A61M 2205/3507* (2013.01); *A61M 2205/3584* (2013.01); *A61M 2205/50* (2013.01); *A61M 2205/502* (2013.01); *A61M 2205/52* (2013.01); *A61M 2205/581* (2013.01); *A61M 2205/8206* (2013.01); *A61M 2210/12* (2013.01); *A61M 2230/005* (2013.01); *A61M 2230/20* (2013.01); *A61M 2230/201* (2013.01)

(58) Field of Classification Search
CPC .... A61M 2230/201; A61M 2005/1726; A61M 2205/33; G01N 33/66; G01N 33/48792; C12Q 1/006
See application file for complete search history.

(56) References Cited

U.S. PATENT DOCUMENTS

| | | | |
|---|---|---|---|
| 6,514,718 B2* | 2/2003 | Heller | C12Q 1/006 205/777.5 |
| 6,544,212 B2 | 4/2003 | Galley et al. | |
| 6,589,202 B1 | 7/2003 | Powell | |
| 6,740,072 B2 | 5/2004 | Starkweather et al. | |
| 7,727,147 B1 | 6/2010 | Osorio | |
| 8,357,145 B2 | 1/2013 | Schleicher et al. | |
| 8,376,984 B2 | 2/2013 | James | |
| 8,562,528 B2 | 10/2013 | Leach et al. | |
| 8,591,498 B2 | 11/2013 | John | |
| 9,037,210 B2 | 5/2015 | Simpson et al. | |
| 2004/0059393 A1* | 3/2004 | Policker | A61K 49/0004 607/40 |
| 2004/0087992 A1 | 5/2004 | Gartstein | |
| 2005/0049177 A1* | 3/2005 | Bachovchin | C07K 14/57563 530/308 |
| 2005/0203001 A1* | 9/2005 | Arbit | A61B 5/14532 514/5.9 |
| 2007/0060971 A1* | 3/2007 | Glasberg | A61N 1/36007 607/40 |
| 2007/0078391 A1 | 4/2007 | Wortley et al. | |
| 2008/0120039 A1* | 5/2008 | Hall | G01N 33/74 702/19 |
| 2008/0183060 A1 | 7/2008 | Steil et al. | |
| 2008/0267925 A1 | 10/2008 | Broytman et al. | |
| 2009/0156988 A1* | 6/2009 | Ferren | G06F 19/00 604/65 |
| 2009/0281519 A1 | 11/2009 | Rao et al. | |
| 2010/0028850 A1* | 2/2010 | Brassil | A01N 1/0247 435/1.2 |
| 2010/0094118 A1* | 4/2010 | Kobayashi | A61B 6/504 600/410 |
| 2010/0269837 A1 | 10/2010 | Levinson et al. | |
| 2012/0245556 A1 | 9/2012 | Kovatchev et al. | |
| 2012/0253190 A1* | 10/2012 | Gauthier | A61B 8/06 600/431 |
| 2012/0329161 A1* | 12/2012 | Everson | A61J 1/05 436/71 |
| 2013/0060139 A1* | 3/2013 | Richter | A61B 5/6876 600/438 |
| 2013/0289370 A1* | 10/2013 | Sun | A61B 5/14532 600/316 |
| 2014/0228715 A1* | 8/2014 | Schroeder | A61B 5/4839 601/2 |
| 2014/0272923 A1* | 9/2014 | Mayer | A01N 1/0247 435/1.2 |
| 2014/0276554 A1 | 9/2014 | Finan et al. | |
| 2015/0148665 A1 | 5/2015 | Sato et al. | |
| 2015/0208950 A1* | 7/2015 | Aki | A61B 5/02007 600/324 |
| 2015/0342177 A1* | 12/2015 | Hassanein | A01N 1/0247 435/284.1 |
| 2016/0015422 A1* | 1/2016 | De Cicco | A61B 8/461 600/439 |
| 2016/0015756 A1 | 1/2016 | Broytman et al. | |
| 2016/0038673 A1 | 2/2016 | Morales | |
| 2017/0049960 A1 | 2/2017 | Ngyyen et al. | |
| 2017/0245943 A1 | 8/2017 | Foster et al. | |
| 2018/0050154 A1 | 2/2018 | Gahan | |
| 2018/0125399 A1 | 5/2018 | Joseph | |
| 2019/0366067 A1 | 12/2019 | Ginggen | |
| 2020/0188577 A1 | 6/2020 | Sipe et al. | |
| 2020/0230211 A1* | 7/2020 | Cherrington | A61K 38/26 |
| 2020/0376290 A1 | 12/2020 | Kim et al. | |

OTHER PUBLICATIONS

Schenk, W G Jr et al. "Direct measurement of hepatic blood flow in surgical patients: with related observations on hepatic flow dynamics in experimental animals." Annals of surgery vol. 156,3 (1962): 463-71. doi:10.1097/00000658-196209000-00013 (Year: 1962).*

Mayo Clinic. "Doppler ultrasound: What is it used for?" Mar. 11, 2011. <https://web.archive.org/web/20140102200804/https://www.mayoclinic.org/doppler-ultrasound/expert-answers/faq-20058452>. (Year: 2011).*

American Diabetes Association: http://diabetes.diabetesjournals.org/content/64/10/3439. Accessed Online: Aug. 15, 2016; 24 pages.

Animas Corp. (Johnson & Johnson): http://www.animascorp.com. Accessed Online: Aug. 15, 2016; 6 pages.

CDC: www.cdc.gov/media/pressre1/2010/r101022.html. Accessed Online: Aug. 15, 2016; 2 pages.

CDC: http://www.cdc.gov/diabetes/statistics/prev/national/figpersons.htm Accessed Online: Aug. 15, 2016; (approached Sep. 2006), 3 pages.

Dana: http://www.danapumps.com. Accessed Online: Aug. 15, 2016; 1 page.

Deltec (Smiths Medical): http://www.cozmore.com. Accessed Online: Aug. 15, 2016; 2 pages.

Disetronic (Roche Healthcare Group): http://www.disetronic.com. Accessed Online: Aug. 15, 2016; 2 pages.

Insulet: http://www.myomnipod.com. Accessed Online: Aug. 15, 2016; 3 pages.

List of IBM Patents or Patent Applications Treated as Related; Date Filed Nov. 22, 2019, 2 pages.

Minimed (Medtronic Diabetes): http://www.minimed.com. Accessed Online: Aug. 15, 2016; 2 pages.

Murphy: "Insulin: Appropriate Placement In the Portal Vein," Advances in Diabetes and Metabolism, Jan. 3, 2014, http://www.hrpub.org, 3 pages.

National Institute of Diabetes: http://diabetes.niddk.nih.gov/dm/pubs/statistics/index.htm#7 (approached Sep. 2006) Accessed Online: Aug. 15, 2016; (approached Sep. 2006), 2 pages.

Nipro Diabetes: http://www.niprodiabetes.com. Accessed Online: Aug. 15, 2016; 1 page.

Shishko et al., "Comparison of Peripheral and Portal (Via the Umbilical Vein) Routes of Insulin Infusion in IDDM Patients," Diabetes, vol. 41, pp. 1042-1049; Sep. 1992.

Up To Date: http://www.utdol.com/utd/content/topic.do?topicKey=diabetes/11100 (approached Sep. 2006); Accessed Online: Aug. 15, 2016; (approached Sep. 2006), 5 pages.

Lindner, O. et al., Scintigraphic Monitoringof Catheter-Port Systems in Type 1 Diabetics with Continuous Insulin Therapy, 2004, Exp Clin Endocrinol Diabetes, 112, 148-152. (Year: 2004).

Mason, T., et al. CHronic Intraperitioneal Insulin Delivery, as compare with subcutaneous delivery, Improves Hepatic Glucose Metabolism in Streptozotocin Diabetic Rats. Nov. 2000, Metabolism, 49(11), pp. 1411-1416. (Year: 2000).

Kessler, et al., "Evaluation of Anticancer Drugs By Bumbilical Vein Hepatography," Cancer: Feb. 1967, vol. 20; pp. 139-322.

McCulloch, et al. "General Principles of Insulin Therapy in Diabetes Mellitus," See http://www.uptodate.com/contents/general-principles-of-insulin-therapy-in-diabetes-mellitus; (approached Sep. 2006); Accessed Online: Aug. 15, 2016; 5 pages.

(56) References Cited

OTHER PUBLICATIONS

White, et al., "Hepatoportography via the Umbilical Vein: A superior Approach to Diagnosis in Liver Disease," Canad. Med. Ass. J., Nov. 13, 1966, vol. 95, No. 20; pp. 997-1003.

* cited by examiner

PORTAL SYSTEM-BASED BIONIC PANCREAS

DOMESTIC PRIORITY

This application is a divisional of U.S. patent application Ser. No. 15/239,262, filed Aug. 17, 2016, the disclosure of which is incorporated by reference herein in its entirety.

BACKGROUND

The present invention relates generally to maintaining glucose homeostasis in diabetic individuals, and more specifically to methods, systems and products including an automated glucose monitoring and insulin administration through the portal venous system.

Diabetes is becoming increasingly more prevalent in the United States. From the years 1980 through 2004, the estimated number of Americans having diabetes more than doubled, increasing from 5.8 million to 14.7 million. Diabetic patients have an increased risk of premature death and can experience severe complications affecting multiple body systems as a result of their condition. The risk of macrovascular (heart or cerebrovascular) complications, for instance, is 2 to 4 times greater among diabetics. Microvascular complications, such as nephropathy, retinopathy, and neuropathy, can also be a major concern. Diabetes, moreover, is the leading cause of new blindness among adults, and results in the majority of non-traumatic lower-limb amputations. Uncontrolled diabetes can provoke acute life-threatening conditions, such as diabetic ketoacidosis and hyperosmolar (nonketotic) coma. Maintaining glucose homeostasis in diabetic individuals while minimizing adverse side effects is increasingly important.

SUMMARY

In accordance with one or more embodiments, a system for maintaining glucose homeostasis is provided. The system includes a pump and a first reservoir including a homeostasis agent. The system also includes an umbilical catheter, the umbilical catheter capable of being advanced in an umbilical vein or in the falciform ligament. The system also includes a sensor. The system also includes a biocompatible coating. The system also includes a microprocessor in communication with the pump and the sensor. The system also includes a power supply.

In accordance with one or more embodiments, a method for maintaining glucose homeostasis is provided. The method includes implanting a pump and reservoir subcutaneously in a patient. The method also includes advancing a catheter including a lumen in the umbilical vein adjacent to the portal vein or in the falciform ligament parallel to the umbilical vein. The method also includes measuring a blood glucose level in the portal venous system and the hepatic arterial system of the patient with a sensor in communication with the pump. The method also includes pumping a homeostasis agent through the catheter based upon the measured blood glucose level. The method also includes administering the homeostasis agent to the portal venous system.

In accordance with one or more embodiments, a method for maintaining glucose homeostasis includes measuring, by a first sensor in communication with a microprocessor, a portal vein blood flow. The method also includes measuring, by a second sensor in communication with the microprocessor, a hepatic artery blood flow. The method also includes calculating a ratio of the portal vein blood flow to the hepatic artery blood flow. The method also includes, based upon the magnitude of the ratio, predicting an increase in a glucose level of a patient.

BRIEF DESCRIPTION OF THE DRAWINGS

The subject matter of the present invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

The invention relates to systems, methods and products for maintaining glucose homeostasis in diabetic individuals. Insulin treatment for glucose homeostasis can be indicated mainly in type 1 diabetes (DM1) or in type 2 diabetes (DM2). DM1 represents 5 to 10% of diagnosed diabetes and is an immune-mediated disease that leads to the destruction of pancreatic beta cells. The majority of patients with DM1 develop the disease early in life. DM1 patients can only survive if regularly treated with exogenous insulin or with pancreas or insulin-secreting beta-cell transplantation. DM2 is often preceded by prolonged insulin resistance followed by beta-cell malfunction. DM2 can be associated with a variety of genetic and environmental factors. The incidence of DM2 among children and adolescents is increasing. Control of disease in most DM2 patients can be accomplished with oral hypoglycemic drugs. However, treatment of many DM2 patients eventually involves insulin treatment.

Figure 1:
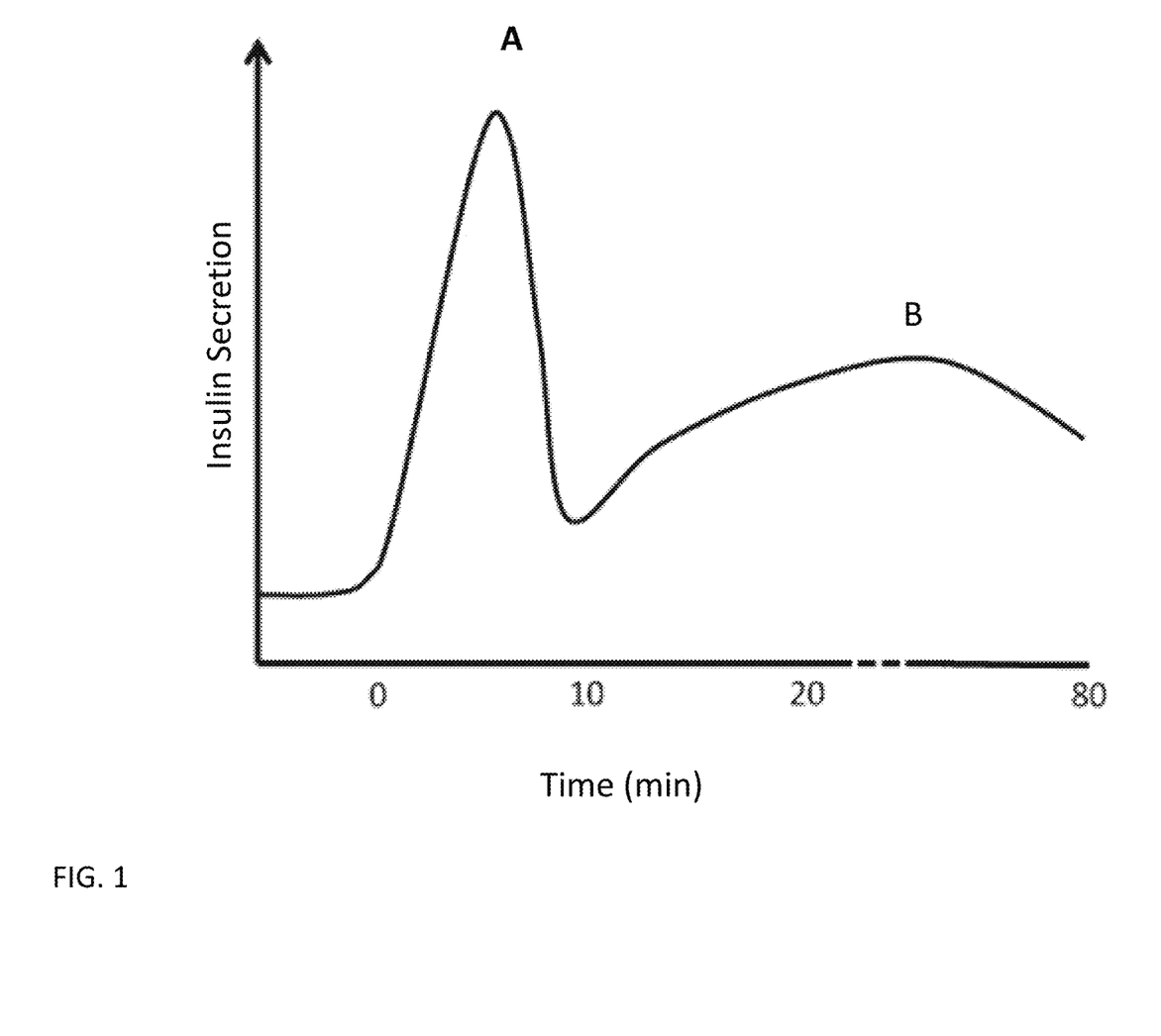
FIG. 1 illustrates a chart characterizing exemplary biphasic insulin secretion.

Insulin secreted by pancreatic beta cells is carried by the portal venous system, where it is transported to the liver and then to the right heart, lungs, and then the systemic circulatory system. Insulin is secreted by beta cells in response to a glucose challenge in a biphasic manner, consisting of a first, immediate phase and a second, prolonged one. FIG. 1 illustrates exemplary biphasic insulin secretion. As is shown, the first phase, designated as region A, involves a relatively sharp increase in insulin secretion over a time of around 10 minutes. The second phase, designated as region B, involves a more gradual increase in insulin secretion with overall insulin levels lower than those seen in the first phase. These phases are preceded by a neural-mediated cephalic phase occurring prior to the rise in plasma glucose. The first phase suppresses hepatic glucose production and results in reduced total insulin needed to yield a similar area under the glucose excursion curve.

About half of the insulin secreted to the portal system can be up-taken by hepatocytes in the first pass. The importance of the first phase response is reflected by the finding that the product of first-phase insulin secretion and insulin sensitivity is constant (known as the "disposition index"). DM2 involves a selective loss of the first phase insulin response.

Insulin is a peptide and thus cannot be administered orally. Conventionally, it can be injected subcutaneously using a syringe and needle, a designated apparatus ("pen") or by an external insulin pump.

Intensive insulin therapy is the mainstay of current therapy for DM1 patients. Intensive insulin therapy leading to improved glycemic control in patients with DM1 can lead to reduced rates of retinopathy, nephropathy, and neuropathy. Intensive insulin therapy can also reduce cardiovascular morbidity and mortality. Intensive insulin therapy involves multiple insulin injections or continuous subcutaneous insulin infusion using an external pump. Intensive insulin therapy, however, can require strict adherence by patients.

Obtaining tight glycemic control in DM1 patients can be complicated by wide glucose excursions, sometimes referred to as "brittle" diabetes. In such patients, frequent plasma glucose checks and multiple daily injections of insulin or use of an insulin pump, can be needed, presenting a formidable challenge for the patient and medical team. Moreover, the resultant reduction in hyperglycemia episodes can be undesirably accompanied threefold increase in the incidence of hypoglycemia. Intensive therapy also can lead to weight gain, which can limit patient compliance.

A goal of insulin delivery is to match circulating insulin to maintain normoglycemia. This can be achieved relatively easily in the fasting state when blood glucose changes very slowly. However, in the postprandial state, plasma glucose levels rapidly rise. When levels of glucose and insulin differ significantly, severe hyperglycemia or hypoglycemia can rapidly occur. In addition to considerations of fasted and fed states, absorption rates of insulin should be considered in insulin therapy. The rate of absorption of subcutaneously-administered insulin absorption is variable, mainly determined by the rate of subcutaneous blood flow. Other factors can influence absorption as well, such as smoking, skin temperature, and massage.

External insulin pumps can also be used in insulin therapy. Continuous subcutaneous insulin therapy, which can be provided by external pumps, can result in better glycemic control compared with multiple daily injections. In this method, basal insulin requirements are supplied by a continuous infusion, with pre-meal bolus doses given to minimize postprandial glucose excursions. In recent years, progress has been made in pump miniaturization, reliability and computing abilities. Nevertheless, treatment using a subcutaneous pump involves an increased risk of hyperglycemia and possibly diabetic ketoacidosis compared to multiple daily injections, potentially owing to mechanical interruptions in insulin flow leading to hypoinsulinemia. It also carries the risk of hypoglycemic episodes which may lead to loss of consciousness. Moreover, patients could feel uncomfortable or embarrassed using insulin pumps. It is estimated that one in three patients will stop using an external insulin pump within 5 years.

There are drawbacks and challenges associated with external insulin pumps. For example, using subcutaneous (SC) glucose sensing and SC insulin administration (an "SC-SC" approach) in a closed loop glycemic control system could present an undesirably long time delay between insulin demand and effective insulin action. This time delay can be, for instance, on the order of 100 minutes from the time of insulin delivery to the peak of a detectable glucose lowering effect. This time is significantly longer than a normal physiological delay, which can be on the order of 30 minutes. The time delay can be the result of many factors, including for example the time of insulin absorption (on the order of 50 minutes with short-acting insulin analogues), the time to insulin action (at least 30 minutes), and interstitial glucose kinetics (on the order of 10 minutes). Once administered, insulin cannot be reabsorbed by the pump. As a consequence, insulin could continue to lower plasma glucose after it is no longer needed. Although control algorithms have been proposed for glucose control by insulin performance, such algorithms suffer drawbacks and are not comparable to that of the endogenous apparatus. To counteract the detrimental time lag in the SC-SC approach, high levels of patient involvement can be required, for instance by involving requesting a patient enter information concerning nutrition and physical activity to assist the pump in determining insulin dosage. A major drawback of SC insulin administration is that, to reach physiologic levels of insulin needed to shut off hepatic glucose production, a higher dose of peripherally administered insulin is required. As about half of endogenously secreted insulin is up-taken by the liver, only about half of the secreted insulin ever reaches the systemic circulation. In contrast, when administered SC, roughly a twofold dose relative to the endogenous dose is required to achieve a high enough insulin level in the liver to inhibit hepatic glucose production. Higher than physiologic insulin levels are harmful in inducing insulin resistance, which contributes to weight gain.

Closed-loop systems including intravenous (IV) monitoring and either intraperitoneal (IP) or IV insulin administration also known but are associated with undesirable delays in insulin function. IV-IP closed loop systems, including intraperitoneal insulin infusions, can have a higher portal/peripheral insulin gradient, more closely approximating physiological conditions. However, delayed action in the IV-IP approach on the order of 70 minutes remains longer than physiological delay, thus glycemic control can be impaired. IV-IV systems can also be used, primarily in critically ill patients. In IV-IV systems, a pump can be implanted under local or general anesthesia in a pocket created in the abdominal wall and secured to the muscular fascia. A disadvantage of systems that require a catheter within the vascular space (venous or arterial) is an associated increased risk for thrombosis or infection.

In case of IP delivery, a catheter is inserted in the peritoneal cavity through a 1-2 cm transmuscular incision in the pocket area, and secured by suturing the catheter flange to the fascia. In case of IV delivery, the catheter is tunneled subcutaneously in the lateral abdomen, inserted into the left subclavian vein, and secured by suturing the catheter flange to the fascia.

The insulin pumps can contain a highly concentrated insulin product which can be replaced in intervals of over a month. A semisynthetic human insulin stabilized with genapol (HOE 21 PH), produced by Hoechst AG (Frankfurt AM, Germany) can be used to avoid aggregation. The pump reservoir can be refilled through a transcutaneous puncture of the central septum of the pump. This can be performed by a trained nurse and does not require local anesthesia, as pain is reportedly minimal.

A surgically implanted programmable insulin pump is available in the European Union and is under investigation in the US. This pump has a sensing means for determining extracellular fluid glucose concentration (subcutaneously) and a catheter for insulin administration (subcutaneously, intraperitoneally or intravenous to a systemic circulation central vein).

In one study, patients treated with an implanted insulin pump were found to have a much lower incidence of severe hypoglycemia (4 versus 33 episodes/100 patient-years with multiple daily injections in patients with type 1 diabetes) compared with other methods of intensive insulin therapy. Moreover, these patients had less day-to-day fluctuation in plasma glucose, less weight gain and better quality of life.

Other implantable venous access systems including a central venous catheter connected to a SC reservoir are known and can allow for prolonged continuous or intermittent drug delivery to the venous system. These instruments are refillable by percutaneous needle puncture.

Insulin administered to the peritoneal cavity can be subsequently predominantly drained by the portal vein, which more closely resembles normal physiologic conditions.

Turning now to an overview of the present invention, one or more embodiments provide systems and methodologies for glucose monitoring and insulin administration to the portal venous system for glucose homeostasis. In some embodiments, the invention includes a catheter placed in the umbilical vein and insulin administration to the umbilical vein using an implantable insulin pump. Cannulation of the obliterated umbilical vein can be used, in some embodiments, to gain permanent access to the portal vein or to the proximity thereof to provide long-term administration of homeostasis agents, such as insulin and glucagon. Embodiments of the invention can provide improved glucose homeostasis, for example, by reducing lag time through administration to the portal circulatory system rather than the systemic circulatory system. Through administration to the portal system, for example, greater control over homeostasis can be exerted through avoiding the loss of homeostasis agents typically associated with administration to the systemic circulatory system. This is because lower insulin doses are required to maintain homeostasis when administered directly to the portal circulation than to the systemic circulation. Through a shorter turnover time and lower insulin doses, reduced rates of treatment and disease-associated complications can be achieved. In some embodiments, the need for homeostasis agents can be anticipated through the use of multiple sensors. For example, comparison of glucose levels at multiple sites, such as the portal vein, hepatic artery and peripheral extracellular space, or measurement of digestive system contents, such as the filling level of the stomach or small intestine can provide an indication of a fasted or fed state, informing the system of an upcoming need for homeostasis agents to regulate blood glucose levels.

Figure 2:
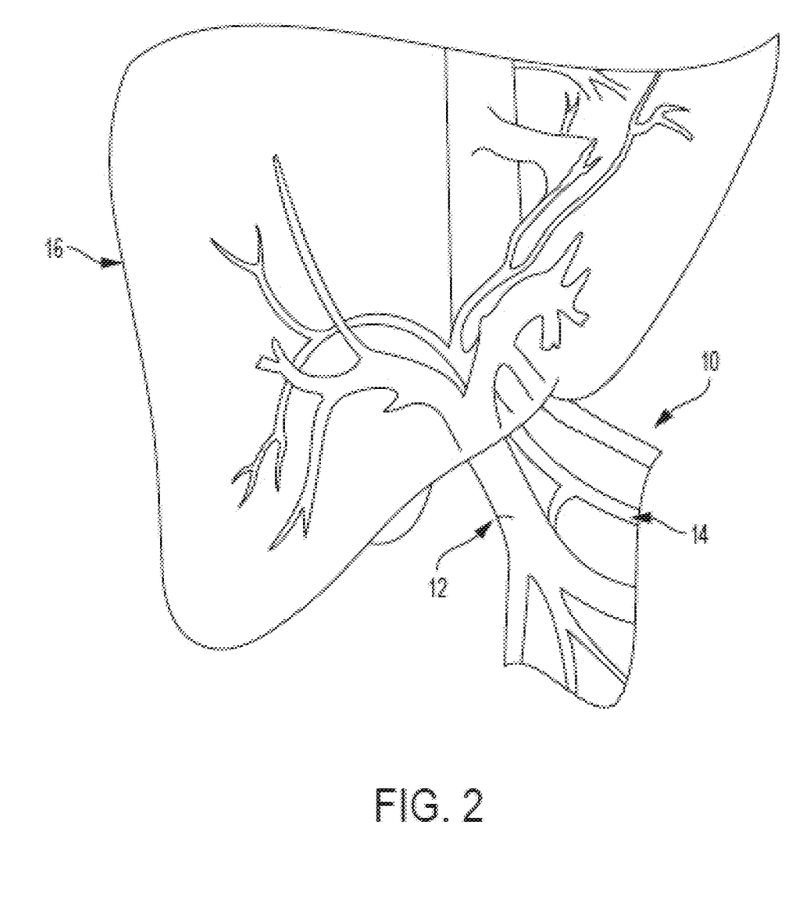
FIG. 2 illustrates cannulation of the umbilical vein.

FIG. 2 illustrates cannulation of the umbilical vein. The umbilical vein 10 connects to the portal vein 12, and carries oxygen and nutrients from the placenta to the embryo. The portal vein 12 and hepatic artery 14 directly access the liver 16.

After birth, following obstruction of the umbilical cord, the umbilical vein collapses. However, the remnant of the umbilical vein can remain patent other than its proximal end just prior to entering the portal vein. Catheterization of the portal vein through the obliterated umbilical vein is known. The umbilical vein can be approached, for example, by making a small incision in the midline, halfway between the umbilicus and xiphoid process (a small extension of the lower part of the sternum). The umbilical vein can be identified as the 3-10 mm diameter collapsed vein within the round ligament. The falciform ligament can run parallel to the umbilical vein.

Figure 3:
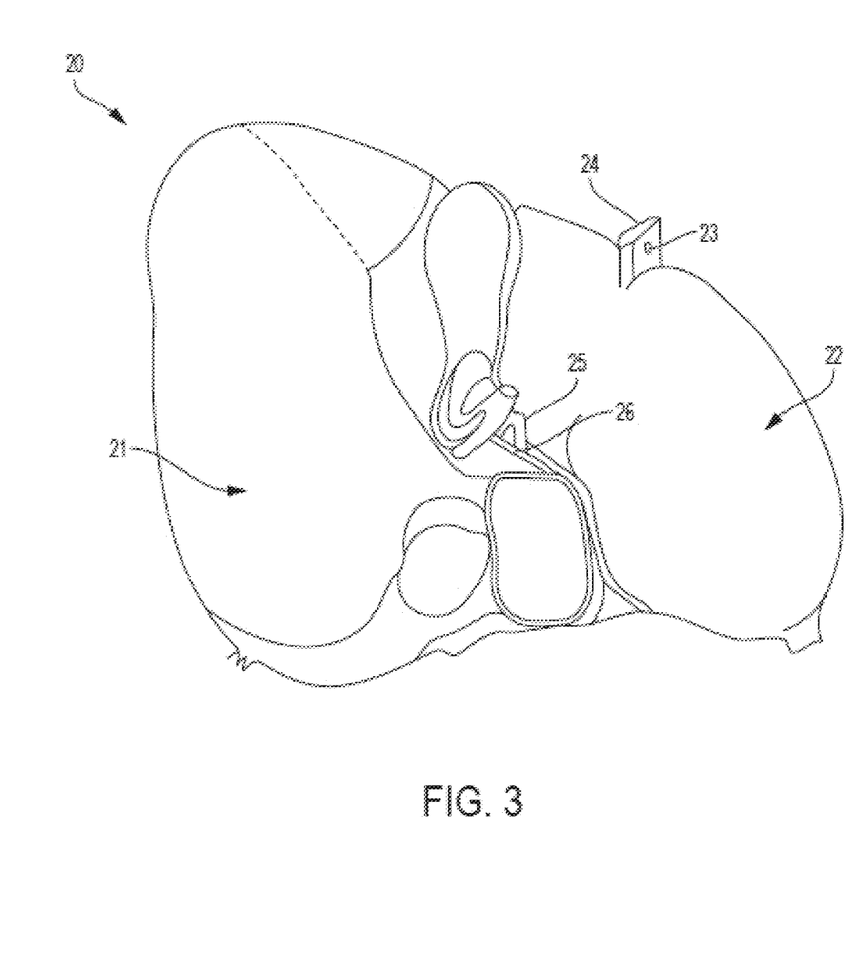
FIG. 3 depicts an illustration of a liver demonstrating the relative position of the falciform ligament.

FIG. 3 illustrates a liver 20 having a right lobe 21 and a left lobe 22. The falciform ligament 23 and round ligament 24 are shown. The falciform ligament 23 and round ligament 24 are located near the hepatic artery 25 and portal vein 26.

Figure 4:
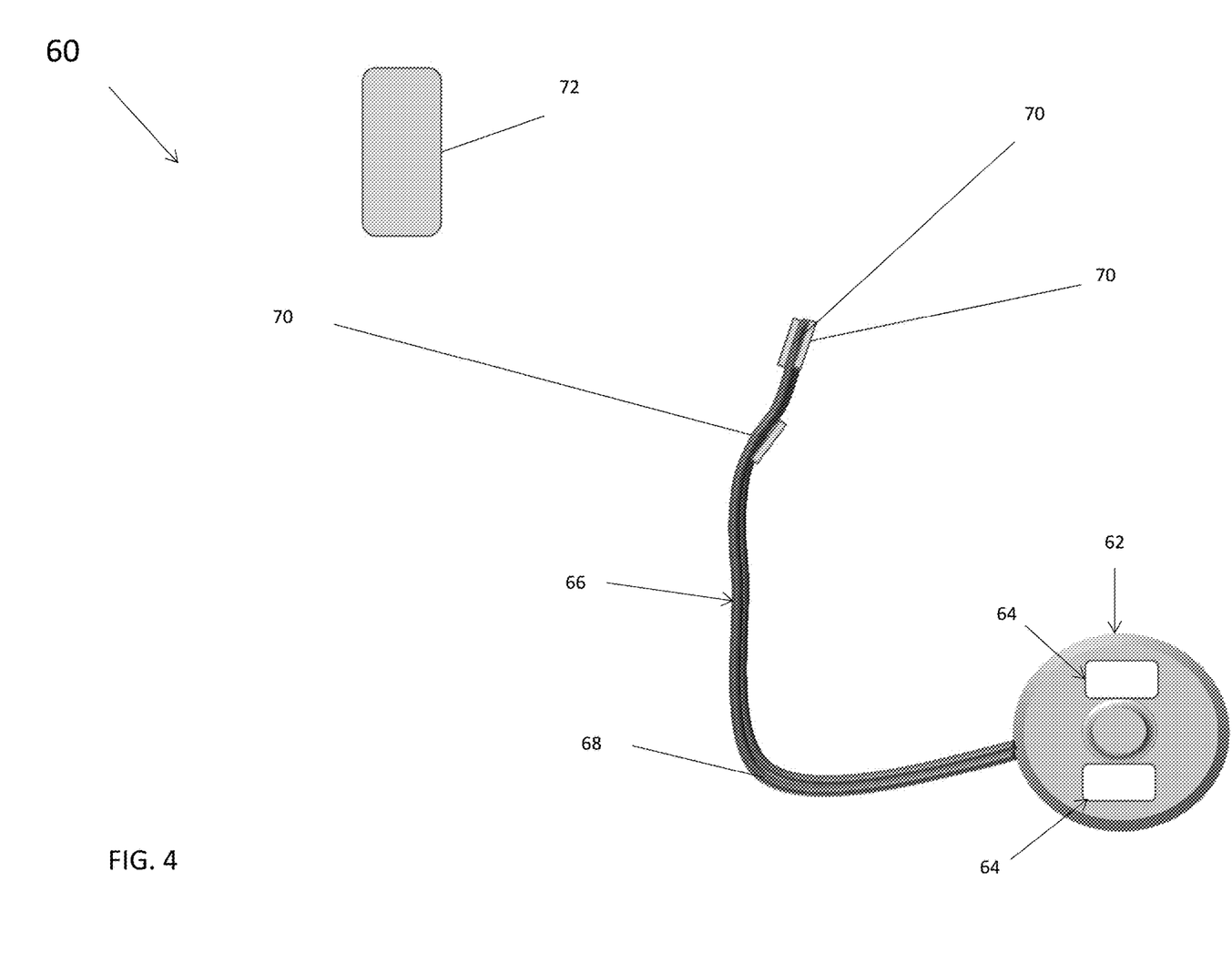
FIG. 4 illustrates a system for maintaining glucose homeostasis according to an embodiment.

FIG. 4 illustrates a system 60 for maintaining glucose homeostasis according to an embodiment. As is shown, the system includes a pump 62 and one or more reservoirs 64. At least one reservoir 64 contains a homeostasis agent. As used herein, homeostasis agent means an agent that can be used to maintain glucose homeostasis, such as insulin, glucagon, glucose, somatostatin, and related hormones and derivatives thereof. Preferably, at least one reservoir 64 contains insulin or an insulin analog. Reservoir 64 is connected to a catheter 66, which contains one or more lumens 68. In some embodiments, reservoir 64 can be refilled using a puncture of the reservoir, including a transdermal puncture of the reservoir either by the patient or by a healthcare professional. The system 60 also includes one or more sensors 70. As is shown, in some embodiments, the system 60 can include an external device 72 in communication with the system, for example in communication with the pump 62. The communication can be a wired or wireless communication. Preferably, the external device 72 communicates wirelessly with the pump 62.

In some embodiments, catheter 66 is an umbilical catheter capable of being advanced in an umbilical vein or in a falciform ligament. In some embodiments, the catheter 66 and lumen 68 are advanced in the umbilical vein or parallel to the umbilical vein within the falciform ligament. The umbilical vein, for example, can be approached through a small midline abdominal incision. In preferred embodiments, the catheter 66 and lumen 68 are guided by imaging, such as ultrasound, computed tomography (CT) imaging, or magnetic resonance (MR) imaging.

The pump 62 can advance a homeostasis agent through a catheter lumen 68. In one embodiment, a homeostasis agent, such as insulin, can be discharged into the umbilical vein, for example in an interstitial space leading to the portal vein. In some embodiments, a homeostasis agent is discharged into the blood, for instance the blood of the portal vein. In one embodiment, the homeostasis agent, such as insulin, can be discharged within the falciform or round ligament and can reach the portal vein or liver tissue by diffusion across the ligament. In another embodiment, the insulin can be discharged across the ligament by way of microneedles transversing the ligament. In an embodiment where insulin is delivered directly to the portal vein, portal blood flow need not be compromised because a relatively small caliber catheter is needed for glucose monitoring an insulin administration. Moreover, in some embodiments, none of the catheter or only the tip of the catheter lies within the portal vein. In some embodiments, insulin is administered to the extracellular fluid adjunct to the portal vein. In one embodiment, a vibrating device, such as an ultrasound transducer, can be used to increase the speed of insulin diffusion across the ligament into the interstitial space or blood stream. In some embodiments, the pump 62 is an insulin pump. In some embodiments, the pump 62 is a glucagon pump.

In some embodiments, the pump includes a highly concentrated insulin product. The insulin product can be replaced at periodic intervals, such as of over a month. In a preferred embodiment, the homeostasis agent is a semisynthetic human insulin stabilized with a non-aggregation agent, such as genapol (HOE 21 PH) produced by Hoechst AG (Frankfurt AM, Germany).

Sensor 70 can be a chemical sensor, an optical sensor, an acoustic sensor or another type of sensor. In a preferred embodiment, the system 60 includes at least one glucose sensor. Glucose sensor can use any known method to detect plasma or extracellular glucose. Preferably, glucose sensor includes a chemical or optical sensor. In one embodiment, spectroscopy is used to determine the level of glucose or another homeostasis agent, such as insulin and related hormones. Preferably, spectroscopy is used to measure the level of glucose or another homeostasis agent within the portal vein or one or more of its contributors or branches. In some embodiments, the system includes a sensor used to measure glucose or other substances within the hepatic artery or one or more of its contributors or branches. In another embodiment, the system includes a sensor capable of monitoring flow across the splenic vein. In some embodiments, measurement of the concentration of glucose or another homeostasis agent is done without the sensor being in contact with blood, such as through the wall of the portal vein or contributors thereof or hepatic artery or branches thereof. In some embodiments, the sensor 70 is a glucagon sensor. In some embodiments, the sensor 70 is an insulin sensor. In some embodiments, the sensor is an acoustic sensor. An acoustic sensor can be capable of monitoring blood flow through a blood vessel, such as portions of the portal vein and hepatic artery.

In one embodiment, a sensor 70 includes an ultrasound. In one embodiment, a sensor 70 includes a Doppler transponder capable of monitoring blood flow within the portal venous system and hepatic arterial system. In one embodiment, a sensor 70 includes a miniature microphone. In some embodiments, system 60 includes a sensor 70 capable of monitoring the flow across a blood vessel, such as the portal vein, hepatic artery, or one or more of their contributors or branches. In some embodiments, system 60 includes a sensor 70 with at least one ultrasound or Doppler transponder or miniature microphone capable of monitoring the content or flow of a digestive component in a digestive region. Digestive component includes, for example, the stomach, the duodenum and/or other portions of the small intestine or the large intestine.

Sensors can include movement sensors, heart rate sensors, EKGs, oxygen saturation sensors, neural excitation detectors, chemoreceptors, such as chemoreceptors reacting to neurohormones including, for instance, cholecystokinin, gastric inhibitory polypeptide, and the like. Sensors can also include activity tracking sensors, such as gyrometers or accelerometers. In some embodiments, activity tracking sensors can detect user activity levels and use such levels to predict anticipated glucose demand. In preferred embodiments, sensors are in communication with a microprocessor.

In one embodiment, the system includes a sensor at the portal vein and a sensor at the hepatic artery. In another embodiment, the system includes a sensor at the portal vein and a sensor at a digestive region.

The external device 72 can include, for example, a telephone, smartphone, smartwatch, PDA, pager, facsimile machine, modem, personal computer, or laptop or an externally designated unit. The external device 72 can be a wired or wireless device. The external device 72 can communicate via a wired communication or wirelessly with one or more components of the system 60. Preferably, the external device 72 communicates wirelessly with the system 60, for example via ultrasound, Bluetooth, or RFID.

In some embodiments, the external device 72 receives a signal including a homeostasis status of a patient or of the system. In some embodiments, the external device 72 provides an output including a homeostasis status of a patient or of the system. The homeostasis status can include any information pertaining to the homeostasis of the patient or of the system, including, for example, the sensed data, the reservoir status, presence or absence of extreme glucose readings, or information concerning device malfunction. The external device 72 can provide a signal to a user concerning a homeostasis status of the patient or of the system. The signal can include any sensory, visual, or auditory output. For example, the external device 72 can vibrate or generate a sound indicating system malfunction. By way of another example, the external device 72 can use an output to a display providing glucose concentration, insulin dosage, or reservoir supply.

In some embodiments, the pump or reservoir can provide a signal to a user. For example, the pump and/or reservoir can use light projected to the skin to display glucose concentration, insulin dosage, or reservoir supply. Light provided by the pump and/or reservoir can also be used to mark the area to be punctured for insulin or other homeostasis agent refill. The pump can also provide alerts using other means, for example sound or vibration.

The system 60 preferably includes a power supply. The power supply can include a long-life battery, rechargeable battery charged by magnetic induction or by ultrasound energy, a micro capacitor, or mechanical or chemical transducers harvesting body energy.

The system 60 can also include a biocompatible coating. For example, it can be advantageous to provide a biocompatible coating to components implanted within a patient. In some embodiments, the catheter contains a biocompatible coating. In some embodiments, the pump contains a biocompatible coating. In some embodiments, the sensors can contain a biocompatible coating.

In some embodiments, the system 60 includes a microprocessor. For example, a microprocessor can be integrated with or in communication with a system pump and/or reservoir. A microprocessor can be capable of capturing, recording, analyzing, and/or reporting data. Preferably, the microprocessor is capable of capturing, recording, analyzing, and reporting data from multiple sensors. In some embodiments, microprocessor integrates input from a plurality of sensors, such as all sensors in a system. In some embodiments, the microprocessor is capable of receiving data from external devices 70, such as external sensors or external devices. In some embodiments, the microprocessor is programmable by a user, such as a remote user.

In some embodiments, the microprocessor calibrates glucose level readings based upon glucose data from one or more sensors. Preferably, the microprocessor determines the need for insulin and signals the pump to distribute the insulin through a lumen.

In some embodiments, the microprocessor operates one or more pumps to administer one or more homeostatic agents or other substances through one or more lumens.

In some embodiments, system 60 includes a plurality of reservoirs. For example, system 60 can include an insulin reservoir and a glucagon reservoir. In a preferred embodiment, in a system including an insulin reservoir and a glucagon reservoir, a microprocessor determines on an ongoing basis whether glucagon is needed and, when needed, signals a pump to distribute the glucagon through a catheter lumen.

Figure 5:
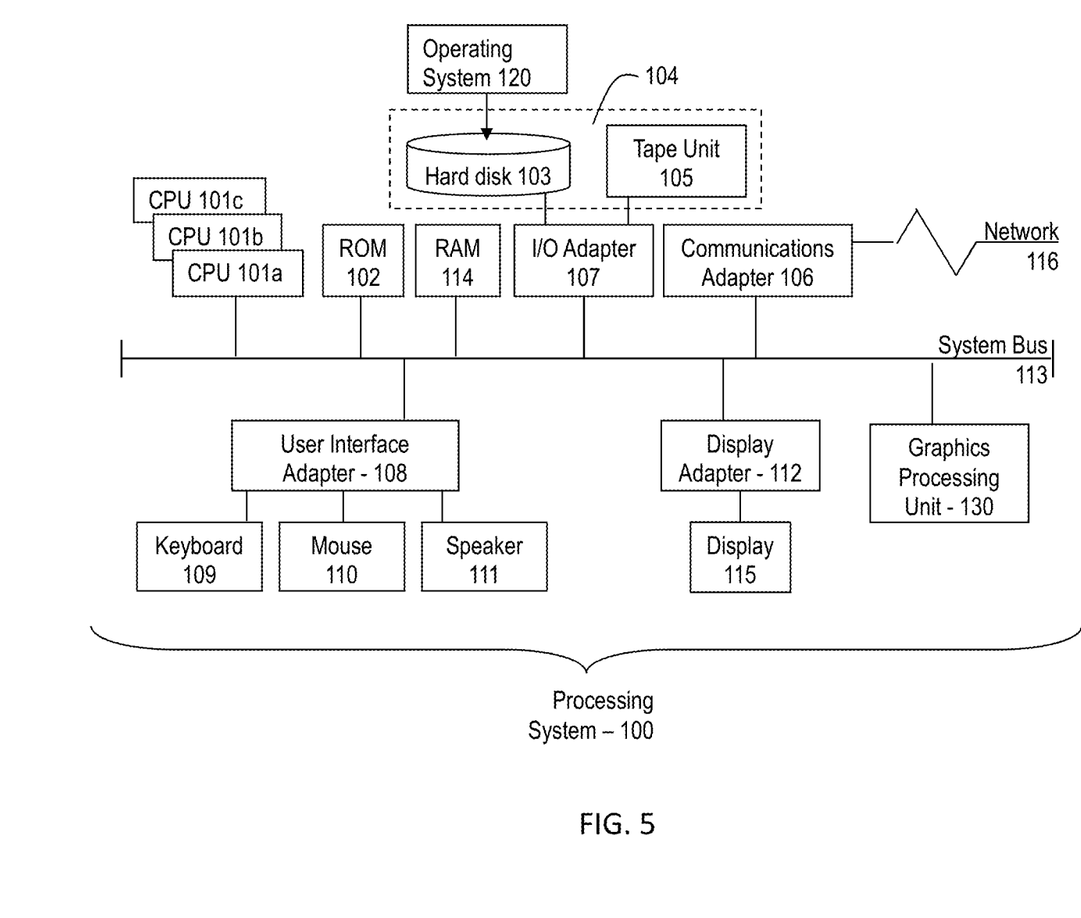
FIG. 5 is a computer system according to one or more embodiments.

Referring to FIG. 5, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 can include a reduced instruction set computer (RISC) microprocessor. Processors 101 are coupled to system memory 114 and various other components via a system bus 113. Read only memory (ROM) 102 is coupled to the system bus 113 and can include a basic input/output system (BIOS), which controls certain basic functions of system 100.

FIG. 5 further depicts an input/output (I/O) adapter 107 and a network adapter 106 coupled to the system bus 113. I/O adapter 107 can be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 can be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which can include a graphics adapter to improve the performance of graphics intensive applications and a video controller. In one embodiment, adapters 107, 106, and 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which can include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 5, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 5.

Figure 6:
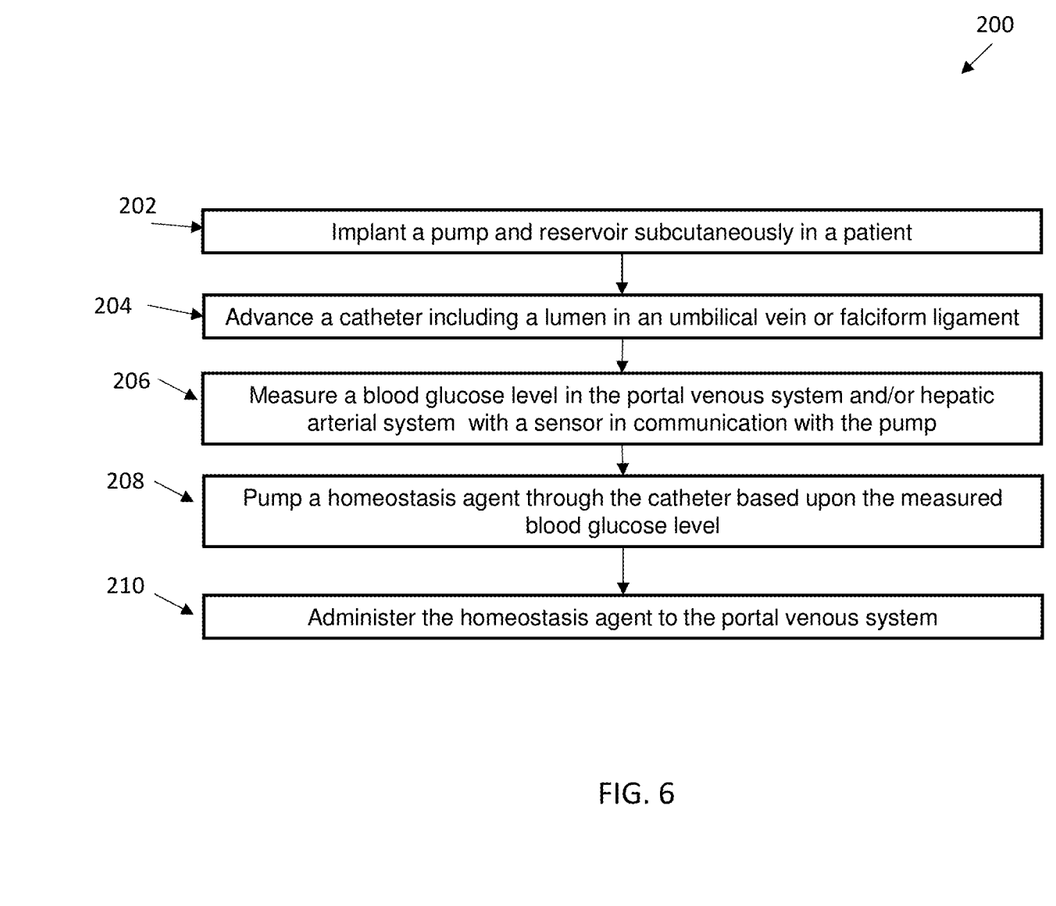
FIG. 6 is a flow diagram illustrating a method for maintaining glucose homeostasis according to an embodiment.

Referring now to FIG. 6, a flow chart illustrating a method 200 for maintaining glucose homeostasis according to an embodiment is shown. As is shown at block 202, the method 200 includes implanting a pump and a reservoir subcutaneously in a patient. For example, the pump and reservoir can be implanted in the subcutaneous area of the abdomen, flank or chest of a patient. The method 200 also includes advancing a catheter including a lumen in an umbilical vein or falciform ligament, as shown at block 204. The umbilical vein can be identified through a midline incision or by use of imaging techniques. In some embodiments a catheter with one or more lumens and one or more sensors is advanced along the umbilical vein without penetration of its obliterated proximal portion where it connects with the portal vein. The distal end of the catheter can be connected to the implanted device after implantation. In one embodiment, administering the homeostasis agent includes discharging insulin into the portal vein or the falciform ligament. The method 200 also includes, as shown at block 206, measuring a blood glucose level in the portal venous system with a sensor in communication with the pump. In some embodiments, a method includes monitoring a blood glucose level in the portal vein or a portion thereof. In some embodiments, a method includes monitoring a blood glucose level in a hepatic artery or a portion thereof. In some embodiments, a method includes monitoring a blood glucose level in vessels connected to the portal vein or the hepatic artery. The method 200 also includes pumping a homeostasis agent through the catheter based upon the measured blood glucose level, as shown at block 208. The method 200 also includes, as shown at block 210, administering the homeostasis agent to the portal venous system. For example, in some embodiments, a homeostasis agent can be automatically administered to the proximal part of the umbilical vein or to the portal vein.

In some embodiments, the method includes monitoring plasma or extracellular fluid glucose.

In some embodiments, the method includes monitoring the content of a digestive component. For example, in some embodiments, the method includes monitoring the content of the stomach, the small intestine, or the large intestine. In some embodiments, input from other sensors is integrated, including gastric sensors, intestinal fullness sensors, flow sensors, portal vein and hepatic artery blood flow sensors, EKG, accelerometers, pH meters, ketone body sensors, heart rate sensors, oxygen saturation sensors, and external data sensors, including, for example, weather sensors, temperature sensors, and the like.

In some embodiments, measurements are made on an ongoing basis. For example, homeostasis agent levels can be automatically determined on an ongoing basis to maintain glucose within a healthy range and avoiding prolonged or excessive hypoglycemia or hyperglycemia.

In some embodiments, the method includes interacting with a user, such as a patient or medical care provider. For example, a method can include reporting a glucose state, hormone inventory, battery charge, or other system parameters to a user. In some embodiments, the method includes modifying the system's computational parameters.

Figure 7:
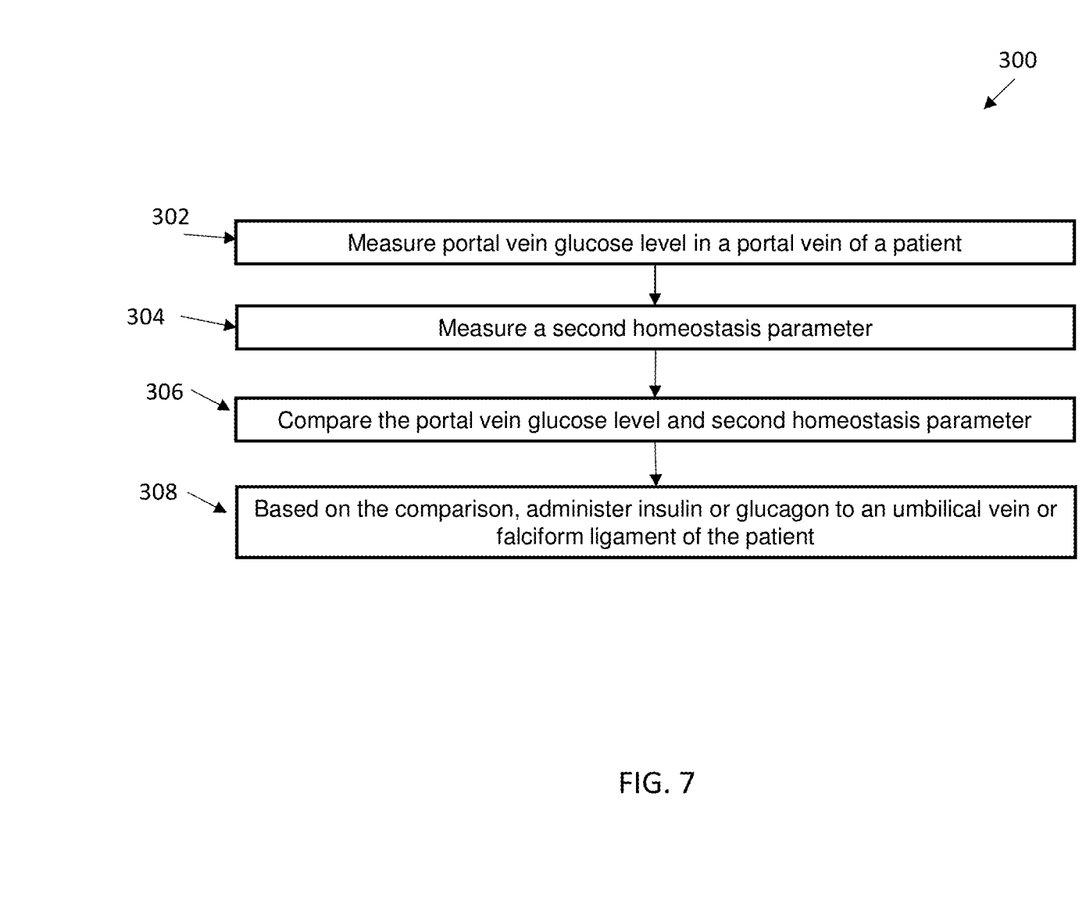
FIG. 7 is a flow diagram illustrating another method for maintaining glucose homeostasis according to an embodiment.

FIG. 7 shows a flow chart illustrating a method 300 for maintaining glucose homeostasis according to another embodiment. As is shown at block 302, the method 300 includes measuring a portal vein glucose level in a portal vein of a patient. The method 300 also includes, as shown at block 304, measuring a second homeostasis parameter. The second homeostasis parameter may be, for example, portal blood flow, hepatic artery blood flow, arterial blood glucose, or combinations thereof. The method 300 also includes comparing the portal vein glucose level and second homeostasis parameter, as shown at block 306. The method 300 also includes, as shown at block 308, administering insulin or glucagon to an umbilical vein or falciform ligament of the patient based on the comparison.

Figure 8:
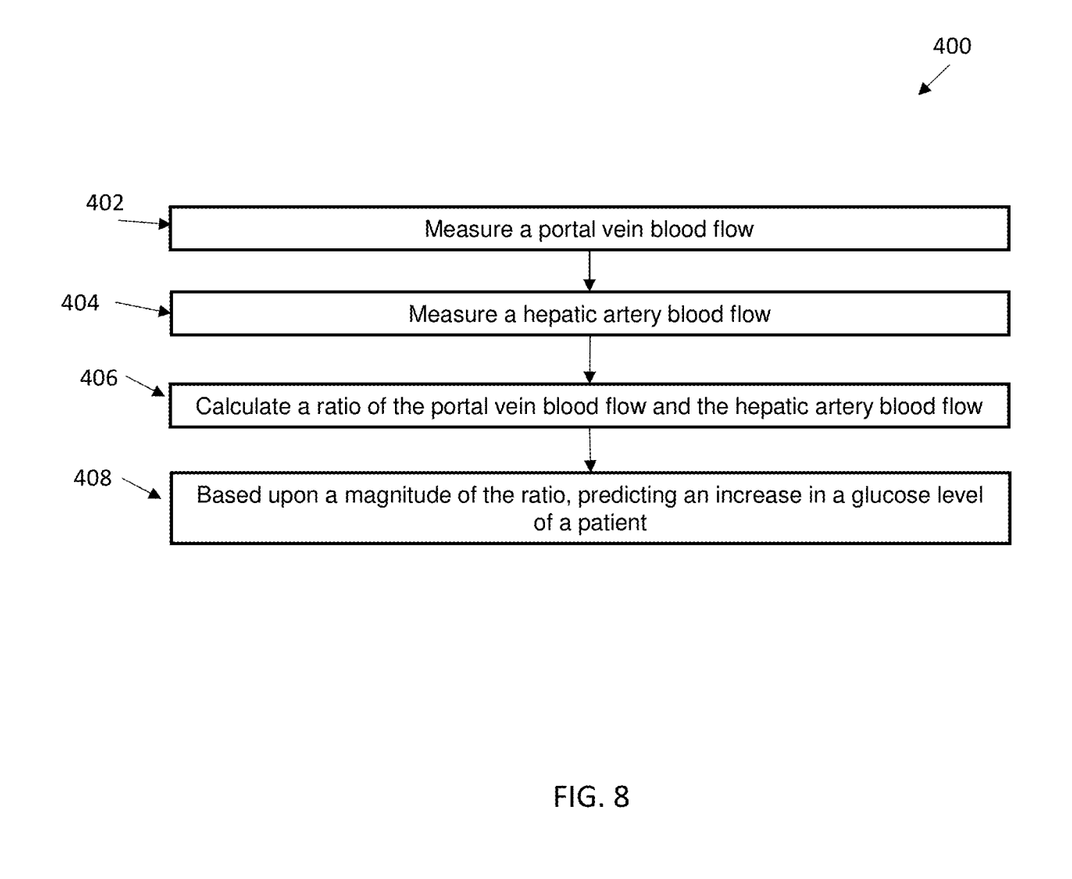
FIG. 8 is a flow diagram illustrating another method for maintaining glucose homeostasis according to an embodiment.

FIG. 8 shows a flow chart illustrating a method 400 for maintaining glucose homeostasis according to another embodiment. As is shown at block 402, the method 400 includes measuring a portal vein blood flow. As shown at block 404, the method 400 also includes measuring a hepatic artery blood flow. The method 400 also includes calculating a ratio of the portal vein blood flow and the hepatic artery blood flow, as shown at block 406. As shown at block 408, the method 400 includes, based upon a magnitude of the ratio, predicting an increase in a glucose level of a patient. For example, a relatively large ratio can indicate that a patient has recently fed, as indicated by differing glucose levels in different regions of the patient's body. An indication that a patient has recently fed can predict an upcoming need for administration of a glucose homeostasis agent to maintain glucose homeostasis. In some embodiments, a method further includes administering, by a pump in communication with a processor, insulin or glucagon to an umbilical vein or falciform ligament of the patient. In some embodiments, measuring the portal vein blood flow and/or hepatic artery blood flow includes using an internal sensor, such as a sensor adjacent to the portal vein and/or hepatic artery. In some embodiments, the sensor(s) is not in contact with a patient's blood flow. In some embodiments, sensor(s) are implanted in an umbilical vein. In some embodiments, sensor(s) are external, such as transdermal sensors. For example, in some embodiments, one or more sensors includes an ultrasound transducer applied over the skin.

In some embodiments, the second homeostasis parameter is a secondary glucose level in a secondary region of the patient. A secondary region of the patient can include, for example, any region that can provide information useful for maintaining glucose homeostasis. For example, a secondary region can include a digestive region. In some embodiments, the second homeostasis parameter includes a stomach content analysis.

In some embodiments, the method includes determining whether the patient is in a fasted or fed state.

In some embodiments, the method includes sending a signal including a homeostasis status to an external device.

Systems and methods according to one or more embodiments can reduce the insulin dosage needed to normalize plasma glucose concentration. For example, umbilical vein glucose sensing coupled with umbilical vein insulin administration can reduce hyperinsulinemia and consequently alleviate insulin resistance. In some embodiments, systems and methods described herein can prevent insulin-induced weight gain.

Systems and methods described herein can also minimize the delay between increased insulin need and insulin supply. This can, for example, reduce post-prandial hyperglycemia and late hypoglycemia that can sometimes result from delayed insulin administration in the SC or IP approaches. In some embodiments, systems described herein can be programmed to elicit an insulin release physiologically equivalent to a biphasic insulin release. Thus, post-prandial hyperglycemia can be eliminated by early HPG shut down. In some embodiments, the system can be programmed to administer insulin prior to glucose absorption in a cephalic response-like manner. For example, sensor input such as brain wave analysis, mastication input, saliva secretion input, or manual user input, can provide advance notice of glucose absorption, prompting early insulin administration.

As will be appreciated by those skilled in the art, systems and methods described herein can demand less cooperation from patients than other glucose homeostasis methods. For instance, intensive insulin administration treatment involves frequent punctures both to determine plasma glucose and to administer insulin. In some embodiments, systems described herein involve relatively infrequent reservoir refilling and the system components can remain in the body for a number of years.

Thus, it can be seen from the forgoing detailed description that one or more embodiments of the present invention provide technical effects and benefits. In some embodiments, systems and methods described herein can improve long-term glycemic control, which could reduce microvascular and macrovascular complications. Thus, the systems and methods described herein could reduce morbidity and increase patient quality of life.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for maintaining glucose homeostasis of a patient, comprising:
measuring, by a first sensor in communication with a microprocessor, a portal vein blood flow, wherein a module has been implanted subcutaneously in the patient, the module comprising a pump, an insulin reservoir, and a glucagon reservoir;
measuring, by a second sensor in communication with the microprocessor, a hepatic artery blood flow;
calculating a ratio of the portal vein blood flow to the hepatic artery blood flow,
based upon a magnitude of the ratio, predicting an increase in a glucose level of the patient, the magnitude of the ratio being an indication that the patient has been fed and has a need for administration of a glucose homeostasis agent to maintain glucose homeostasis; and
in response to the indication, administering, by the pump implanted in the patient and in communication with the microprocessor, insulin or glucagon through a tip of an implanted catheter, positioned in a falciform ligament of the patient, to a portal vein of the patient, wherein only the tip of the implanted catheter connected to the pump extends within the portal vein of a portal venous system, wherein no other catheter is connected to the pump.

2. The method of claim 1, wherein the first sensor does not come into contact with the portal vein blood flow.

3. The method of claim 1, wherein the second sensor does not come into contact with the hepatic artery blood flow.

4. The method of claim 1, wherein at least one of the first sensor and the second sensor is implanted in an umbilical vein.

5. The method of claim 1, the method further comprising conducting a stomach content analysis.

6. The method of claim 1, further comprising determining whether a patient is in a fasted state or fed state.

7. The method of claim 6, wherein determining whether the patient is in a fasted state or fed state is based at least in part on the magnitude of the ratio.

8. The method of claim 7, wherein a large value for the magnitude of the ratio indicates that the patient has recently fed.

9. The method of claim 1, wherein at least one of the first sensor and the second sensor comprises a transdermal sensor.

10. The method of claim 9, wherein at least one of the first sensor and the second sensor comprises an ultrasound transducer.

11. The method of claim 1 further comprising sending a signal including a homeostasis status to an external device.

12. The method of claim 1, wherein administering insulin or glucagon to the patient further comprises discharging the insulin or glucagon out of a distal end opening of a lumen of the implanted catheter.

13. The method of claim 1, wherein the first sensor and the second sensor are in a lumen of the implanted catheter.

* * * * *